US010916155B1

(12) United States Patent
Benasich et al.

(10) Patent No.: US 10,916,155 B1
(45) Date of Patent: Feb. 9, 2021

(54) METHOD AND APPARATUS FOR CONSTRUCTING AND/OR USING SALIENTLY PATTERNED SPATIOTEMPORAL INPUTS THAT SUPPORT THE DEVELOPMENT AND MAINTENANCE OF THE NEURAL CIRCUITRY CRITICAL TO EFFICIENT LANGUAGE PROCESSING

(71) Applicant: RAPT Ventures, Inc., New York, NY (US)

(72) Inventors: April A. Benasich, New York, NY (US); Julia M. Whitehead, New York, NY (US)

(73) Assignee: RAPT Ventures, Inc., New York, NY (US)

(*) Notice: Subject to any disclaimer, the term of this patent is extended or adjusted under 35 U.S.C. 154(b) by 0 days.

(21) Appl. No.: 16/946,174

(22) Filed: Jun. 9, 2020

(51) Int. Cl.
*G09B 5/04* (2006.01)
*G06F 3/16* (2006.01)

(52) U.S. Cl.
CPC ............... *G09B 5/04* (2013.01); *G06F 3/165* (2013.01)

(58) Field of Classification Search
CPC ...................................... G09B 5/04; G06F 3/16
See application file for complete search history.

(56) References Cited

U.S. PATENT DOCUMENTS

| | | | |
|---|---|---|---|
| 8,231,543 B2* | 7/2012 | Benasich | G09B 5/04 600/559 |
| 8,951,206 B2* | 2/2015 | Benasich | G09B 5/04 600/559 |
| 9,320,458 B2* | 4/2016 | Benasich | A61B 5/6896 |
| 2017/0046971 A1* | 2/2017 | Moreno | G09B 19/00 |

OTHER PUBLICATIONS

Cantiani et. al., Auditory discrimination predicts linguistic outcome in Italian infants with and without risk for language-learning impairment, Developmental Cognitive Neuroscience, vol. 20, pp. 23-34 (Year: 2016).*

(Continued)

*Primary Examiner* — Eddy Saint-Vil
(74) *Attorney, Agent, or Firm* — Wiggin and Dana LLP; Thomas M. Landman

(57) ABSTRACT

The invention provides for the generation and output of a plurality of spatiotemporally organized, patterned sound streams that, while soothing, also address the critical need for infant brains to attend to salient acoustic cues in the environment—even during sleep—to facilitate the formation of neuronal connections which are essential for later efficient language processing. The algorithmic auditory sequences that comprise the sound streams are designed to engage the auditory cortex in a beneficial way that supports both development and maintenance of linguistic brain circuitry. Sound sequences constructed according to the invention also support continued fine-tuning of similar neuronal connections in adults. In other embodiments, light patterns can be structured to integrate with the sound patterns to further enhance the integrity of the brain's language processing neural circuitry.

7 Claims, 7 Drawing Sheets

Plot Spectrum of "Birds with Stream" using a Hann Window

(56) References Cited

OTHER PUBLICATIONS

Erickson et al., Influences of Background Noise on Infants and Children, vol. 26 issue: 5, pp. 451-457 Article first published online: Oct. 10, 2017; Issue published: Oct. 1, 2017 (Year: 2017).*
Novitski et al., Effects of Acoustic Gradient Noise from Functional Magnetic Resonance Imaging on Auditory Processing as Reflected by Event-Related Brain Potentials, NeuroImage 14, 244-251 (2001) (Year: 2001).*
Benasich AA & Tallal P (2002). Infant discrimination of rapid auditory cues predicts later language impairment. Behavioral Brain Research, 136 (1), 31-49.
Benasich AA, Choudhury, NA, Realpe-Bonilla, T, Roesler CP.(2014). Plasticity in developing brain: active auditory exposure impacts prelinguistic acoustic mapping. Journal of Neuroscience, 34, 40, 13349-13363. doi: 10.1523/JNEUROSCI.0972-14.2014.
Bao S, Chang EF, Davis JD, Gobeske KT, Merzenich MM.(2003). Progressive degradation and subsequent refinement of acoustic representations in the adult auditory cortex. J Neurosci. Nov. 26;23(34):10765-75. doi: 10.1523/JNEUROSCI.23-34-10765. 2003. PMID: 14645468.
Cantiani C, Riva V, Piazza C, Bettoni R, Moltini M, Choudhury N, Marino C & Benasich AA. (2016). Auditory discrimination predicts linguistic outcome in Italian infants with and without risk for language-learning impairment. Developmental Cognitive Neuroscience. 20, 23-34. doi: 10.1016/j.dcn.2016.03.002.
Chang EF & Merzenich MM (2003). Environmental noise retards auditory cortical development. Science, 300:5618: 498-502. doi: 10.1126/science.1082163.
Choudhury N & Benasich AA (2011). Maturation of Auditory Evoked Potentials from 6 to 48 months: Prediction to 3 and 4 year Language and Cognitive Abilities. Clinical Neurophysiology, 122, 2, 320-338. (doi:10.1016/j.clinph.2010.05.035).
Erickson LC, Newman RS (2017) Influences of background noise on infants and children. Curr Dir Psychol Sci. 2017 ; 26(5): 451-457. doi:10.1177/0963721417709087.
Fitch RH, Read H, Benasich, AA (2001) Neurophysiology of speech perception in normal and impaired systems. In A. Jahn & J. Santos-Sacchi (Eds.), Physiology of the ear (2nd ed., pp. 651-672). San Diego: Singular Publishing Group, Inc.
Howard Hughes Medical Institute. "White Noise Delays Auditory Organization In Brain." ScienceDaily. ScienceDaily, Apr. 18, 2003. <www.sciencedaily.com/releases/2003/04/030418081607.htm>.
Lahav A, Skoe E (2014) An acoustic gap between the NICU and womb: a potential risk for compromised neuroplasticity of the auditory system in preterm infants. Front Neurosci. Dec. 5;8:381. doi: 10.3389/fnins.2014.00381.eCollection 2014.
Musacchia, G., Ortiz-Mantilla, S., Realpe-Bonilla, T., Roesler, C.P., Benasich, A.A. Infant Auditory Processing and Event-related Brain Oscillations. J. Vis. Exp. (101), e52420.
Neuroplan. "Does white noise for babies have consequences?" Jul. 15, 2017. https://neuroplan.ca/white-noise-for-babies/.
Zhang LI, Bao S, Merzenich MM (2002) Disruption of primary auditory cortex by synchronous auditory inputs during a critical period. Proc Natl Acad Sci U S A 99:2309-2314. CrossRef Medl.
Dang-Vu TT, Desseilles M, Peigneux P, Maquet P. A role for sleep in brain plasticity. Pediatr Rehabil. Apr. 2006; 9(2): 98-118.
Wang G, Grone B, Colas D, Appelbaum L, Mourrain P. Synaptic plasticity in sleep: learning, homeostasis and disease. Trends Neurosci. Sep. 2011; 34(9): 452-63.

* cited by examiner

Frequency vs. time 10⁴ complex waveform of "White Gaussian Noise"

Frequency vs. time complex waveform of 10 sec of full-spectrum "White Noise"

Frequency vs. time complex combined waveform of the sequence "Birds with Stream"

Frequency vs. time linear spectrogram of "Birds with Stream"

Frequency vs. time log spectrogram of "Birds with Stream"

Plot Spectrum of "Birds with Stream" using a Hann Window

Frequency vs. time complex combined 180 sec waveform of the sequence "Owls, Frogs, Crickets with Stream"

Frequency vs. time complex combined 80 sec waveform of the sequence "Nature mix with Stream"

Frequency vs. time complex waveform of "Twinkle, Twinkle, Little Star"

28-channel spectral analysis, using Short-time Fourier transform (STFT), of children's song "Twinkle, Twinkle, Little Star" for comparison

METHOD AND APPARATUS FOR CONSTRUCTING AND/OR USING SALIENTLY PATTERNED SPATIOTEMPORAL INPUTS THAT SUPPORT THE DEVELOPMENT AND MAINTENANCE OF THE NEURAL CIRCUITRY CRITICAL TO EFFICIENT LANGUAGE PROCESSING

FIELD OF THE INVENTION

This invention relates to a novel method, apparatus and system for supporting the development and maintenance of neural circuitry critical to efficient language processing.

BACKGROUND

The ability to decode speech is dependent upon the accurate perception of successive rapidly presented sounds that occur within as few as tens of milliseconds of each other (Benasich A A & Tallal P (2002). *Infant discrimination of rapid auditory cues predicts later language impairment. Behavioral Brain Research,* 136 (1), 31-49; Musacchia G, Ortiz-Mantilla S, Realpe-Bonilla T, Roesler C P, Benasich A A (2015). *Investigating infant auditory processing and event-related brain oscillations. J Vis Exp* 101:e52420. Medline; Fitch R H, Read H, Benasich, A A (2001). *Neurophysiology of speech perception in normal and impaired systems.* In A. Jahn & J. Santos-Sacchi (Eds.), *Physiology of the ear* (2nd ed., pp. 651-672). San Diego: Singular Publishing Group, Inc.). To support this decoding, one of the critical functions of the developing brain is the construction of an acoustic representation or brain "map" of all the sounds that comprise a child's native language. That map consists of different groups of interconnected neurons which fire together in response to the individual sounds within an incoming language stream, thus facilitating the automatic processing of language. To develop the neural interconnections which underpin these critical language maps, the infant brain must first pay attention to the very small and rapid successive changes in sound that occur in its environment; recognizing these transitions causes the infant to focus on acoustic cues that differentiate individual speech sounds and encourages the infant's developing brain to create tight connections among the groups of particular neurons that must fire together to correctly and automatically process each sound.

As reported in Musacchia et al. (2015 J Vis Exp) and in Fitch et al. (2001 Physiology of the Ear (2nd ed.)), researchers have demonstrated that infants as young as two months old can discriminate rapid (e.g., <100 msec) frequency changes "suggesting that the 'hardware' for detecting the difference between two acoustically similar syllables is in place." Further, as they mature, infants become more proficient at discriminating even finer differences among sounds, specifically they "develop categorical perception, and exhibit cortical specialization for sounds of the native language syllables." Finally, and critically, as multiple studies from Benasich and colleagues have shown, an infant's ability to process very small and rapid changes in simple non-speech sounds (e.g., tones) can predict the language and cognitive performance of 3- and 4-year olds (Choudhury N & Benasich A A (2011). *Maturation of Auditory Evoked Potentials from 6 to 48 months: Prediction to 3 and 4 year Language and Cognitive Abilities. Clinical Neurophysiology,* 122, 2, 320-338. doi:10.1016/j.clinph.2010.05.035); Musacchia et al. 2015; Cantiani C, Riva V, Piazza C, Bettoni R, Moltini M, Choudhury N, Marino C & Benasich A A. (2016). *Auditory discrimination predicts linguistic outcome in Italian infants with and without risk for language-learning impairment. Developmental Cognitive Neuroscience.* 20, 23-34. doi: 10.1016/j.dcn.2016.03.002).

Benasich has also shown that even passive engagement by infants with spectro-temporally-modulated non-speech, that is sounds that are not language but contain acoustic cues pertinent to linguistic decoding, can bootstrap the processing of native speech and facilitate the establishment of the accurate and enduring phonemic representations necessary for optimal acoustic processing (Benasich A A, Choudhury, N A, Realpe-Bonilla, T, Roesler C P (2014). *Plasticity in developing brain: active auditory exposure impacts prelinguistic acoustic mapping. Journal of Neuroscience,* 34, 40, 13349-13363. doi: 10.1523/JNEUROSCI.0972-14.2014). In contrast, sustained exposure by infants to temporally disorganized sound patterns or artificially constrained slices of the acoustic environment can have the reverse effect, disrupting critical pre-linguistic acoustic mapping and potentially impairing later language processing. In animal studies for example, Zhang et al. (Zhang L I, Bao S, Merzenich M M (2002). *Disruption of primary auditory cortex by synchronous auditory inputs during a critical period. Proc Natl Acad Sci USA* 99:2309-2314. Cross Ref Medline) have shown that "exposure to repetitive pure tones" such as pulsed "white noise" (white noise here is defined as a random signal that often contains many frequencies but, even if filtered, has equal intensity at each differing frequency which produces a constant power spectral density (see FIGS. 1*a-b*)) resulted in a deteriorated tonotopy (i.e., a degradation of the anatomic organization by which sound frequencies are registered by particular receptors in the ear and then travel along specialized pathways to specific locations in the brain), supporting the researchers' contention that the development of processing by the primary auditory cortex "is powerfully affected by the spectro-temporal input structures delivered from the acoustic environment during a critical period of postnatal development."

However, infants may not always be exposed to the "spectro-temporal input structures" most beneficial to their development; in fact, the converse is often true. For instance, the previously mentioned white noise is frequently used as a sleep aid for young infants by parents who are likely unaware that Zhang and others have highlighted its potential negative impacts on infant language development (Erickson L C, Newman R S (2017). *Influences of background noise on infants and children. Curr Dir Psychol Sci.* 2017; 26(5): 451-457. doi:10.1177/0963721417709087; Howard Hughes Medical Institute. *"White Noise Delays Auditory Organization In Brain." ScienceDaily.* ScienceDaily, 18 Apr. 2003. <www.sciencedaily.com/releases/2003/04/030418081607.htm>.; Lahav A, Skoe E (2014). *An acoustic gap between the NICU and womb: a potential risk for compromised neuroplasticity of the auditory system in preterm infants. Front Neurosci.* December 5; 8:381. doi: 10.3389/fnins.2014.00381. eCollection 2014; Neuroplan. "Does white noise for babies have consequences?" Jul. 15, 2017. https://neuroplan.ca/white-noise-for-babies/; Zhang et al. 2002). Moreover, even though some research indicates that, for adults, sustained exposure to white noise is not harmful, other research suggests that such exposure may not be entirely benign. For example, Bao et al. demonstrated that in the adult rat brain, two hours of daily pulsed white noise, presented under certain conditions, can degrade functional organization of the primary auditory cortex (Bao S, Chang E F, Davis J D, Gobeske K T, Merzenich M M (2003). *Progressive degradation and subsequent refinement of* acoustic representations in the adult auditory cortex. *J Neurosci.* November 26; 23(34):10765-75. doi: 10.1523/JNEUROSCI.23-34-10765.2003. PMID: 14645468).

Additionally, Lahav and Skoe have documented the negative impacts to the development of auditory processing faced by infants in Neonatal Intensive Care Units ("NICUs"), which are characterized by high frequency ("HF"), noisy environments. According to the two, "[o]verexposure to HF noise during critical periods disrupts the functional organization of auditory cortical circuits. As a result, . . . the ability to tune out noise and extract acoustic information . . . may be impaired, leading to increased risks for a variety of auditory, language, and attention disorders" (Lahav and Skoe, 2014). In other work, Chang and Merzenich (Chang E F & Merzenich M M (2003). *Environmental noise retards auditory cortical development. Science,* 300:5618: 498-502. doi: 10.1126/science.1082163) have shown that rats raised in continuous moderate-level noise environments were delayed in their refinement of response selectivity far beyond normal benchmarks, positing that such effects were "due to deprivation of the instructive nature of saliently patterned spatiotemporal inputs."

Given the importance of supportive acoustic environments to the development and maintenance of optimal auditory and language processing, it would benefit infants, and even adults—during sleep or while awake—to be exposed to appropriately structured sound streams in place of (while still serving the same purpose as) less beneficial acoustic streams such as white noise, or to augment and enhance patterned sound environments inherently less supportive of optimal brain development (e.g., continuous TV input or high levels of background noise).

BRIEF SUMMARY OF THE INVENTION

In order to mitigate the potential negative impacts on infant language development and the potential degradation of the functional organization of the primary auditory cortex in both infants and adults resulting from exposure to "white noise" and HF noisy environments, or otherwise provide a supportive environment for the development and maintenance of language processing capabilities, this invention presents a method, apparatus and system for constructing and/or using saliently patterned spatiotemporal inputs that support the development and maintenance of the neural interconnections critical to efficient language processing which can be used to replace or mask white or HF noise and/or supplement other less beneficial sound environments.

The invention provides for an acoustic environment, during sleep or wake, that is soothing but is also specifically constructed to tune the developing brain to detect and pay attention to the critical tens of milliseconds sound transitions that will later help a child identify sounds that are language, thus enhancing the child's ability to then appropriately map the sounds of his/her native language. The acoustic environment generated by the invention is also of benefit to adults who, particularly as they age and lose sensitivity in the higher frequencies, must continue to attend to sound transitions for efficient language processing. The invention may, in preferred embodiments, consist of a recording, software program or digital audio stream played on an audio output device including such products as smart speakers, portable sound machines such as "soothers," mobile phones, tablets or computers (with or without earphones) in which a structured, mixed frequency carrier sound envelope (the "carrier envelope") plays for a specified interval during which a structured audio pattern (the "auditory sequence") is layered into the carrier envelope to produce a combined sound steam that heightens the developing brain's attention to sound cues that might be language. The structured auditory sequence includes both a "standard" repeating sound and a contrasting infrequently presented "novel" sound (or sounds) that deviates in frequency, duration, modulation, and/or pattern from the standard sound; the standard and novel sounds are presented at pseudorandom intervals within the auditory stream and then the entire sequence is layered into the carrier envelope (see FIG. 3). When employed during sleep or wake, the invention serves as a passive sound enhancement environment. Exposure to this rich and unpredictably varying acoustic environment is particularly beneficial to a child's developing brain and ongoing language development and also supports and maintains phoneme-based language processing ability in children and adults.

BRIEF DESCRIPTION OF THE DRAWINGS

The features and advantages of this disclosure will be more fully understood with reference to the following, more detailed description, when taken in conjunction with the accompanying figures.

FIG. 1*a* shows a frequency vs. time complex waveform of White Gaussian Noise and FIG. 1*b* shows a close-up view of the frequency vs. time complex waveform of full-spectrum White Noise over a period of 10 seconds.

FIG. 4*a* illustrates the sequence as a frequency vs. time complex combined waveform; FIG. 4*b* illustrates the sequence as a frequency vs. time linear spectrogram; and FIG. 4*c* illustrates the sequence as a frequency vs. time log spectrogram.

FIG. 6*a* illustrates a frequency vs. time complex combined 180 sec waveform of an additional exemplary sequence, "Owls, Frogs, Crickets with Stream" in accordance with this disclosure; FIG. 6*b* illustrates a frequency vs. time complex combined 80 sec waveform of an additional sequence, "Nature mix with Stream" in accordance with this disclosure; FIG. 6*c* illustrates, as a comparative example, a frequency vs. time complex waveform of "Twinkle, Twinkle, Little Star"; and FIG. 6*d* illustrates, as a comparative example, a 28-channel spectral analysis, using a Short-time Fourier transform (STFT), of the children's song "Twinkle, Twinkle, Little Star."

DETAILED DESCRIPTION

Figure 1A:
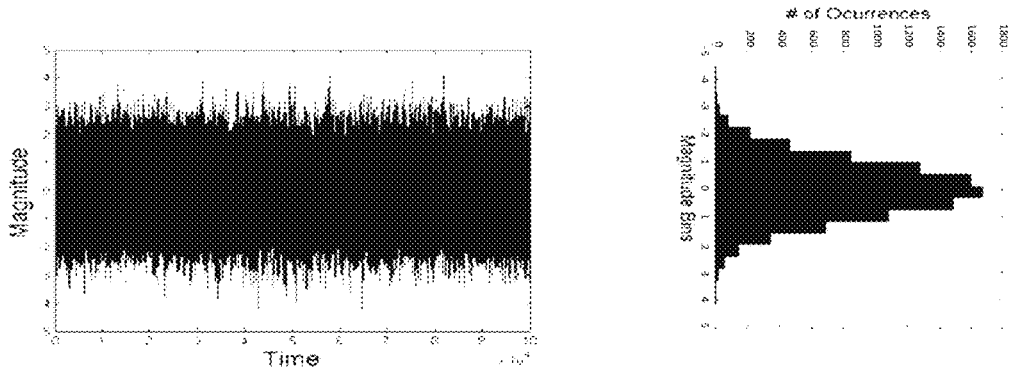
FIGS. 1*a* and 1*b* illustrate the constant power spectral density of white noise.

The disclosed invention provides ordered non-linguistic auditory sequences with acoustic cues that are similar to the tens of milliseconds changes characteristic of all languages and modulates these sounds in order to engage the attention of the developing brain. That is, these auditory sequences include variations and transitions in the tens of millisecond range, which are language-like but not language. More specifically, the sequences consist of changing sounds comprised of a plurality of standard sounds, designed to meet particular audio parameters, followed at a specified interval by a plurality of novel deviant sounds (i.e., new sounds that are different from the standard sounds preceding them and also designed to meet particular parameters for such deviant sounds) with the sounds varying from easily detectable to difficult to discern.

These discrete auditory sequences are embedded in background or "carrier" sound envelopes that can vary from 2-10 minutes long and then repeat. Each carrier sound envelope is a pleasing, continuous and soothing sound pattern that does not have extensive peaks and valleys but occurs within a predetermined restricted range. The carrier envelope may contain sounds that mimic many types of naturally occurring or constructed sound scenes (e.g., crickets and birds, ocean waves, wind, tonal music patterns, etc.) that have a variability and range that fits within the algorithmic requirements.

In total, the system is designed to generate a plurality of spatiotemporally organized auditory sequences or "auditory scenes" based on the algorithm described herein, which is designed to engage the auditory cortex in a beneficial way that supports early brain development in children and language processing in children and adults. The sounds that comprise the acoustic patterns that make up the auditory scenes have specific parameters. Each sound in the auditory sequence is limited in length and short in duration. Specifically, the standard and novel sounds contain acoustic cues including interspersed gaps, transitions or inter-stimulus intervals (ISIs) within each sound that can vary from about 2 to about 300 ms in duration. Such discrete sound cues, although not language themselves, fit the parameters of linguistic or language-like sounds. At least one such auditory sequence, of a plurality of auditory sequences, is then embedded within at least one of a plurality of structured carrier sound envelopes.

The structured and mixed frequency carrier sound envelopes are comprised of at least one audio stream of a plurality of complex audio streams, with continuous, rhythmic variation of selected parameters, at the chosen frequency range, but within the specified range of 40-10,000 Hz with all sounds at 75 db or lower in intensity. Total duration of the overall sequence can be between 2 and 10 minutes and then repeated (1 to N times).

The auditory sequences embedded in the carrier envelopes may be a sequence of auditory stimuli (i.e., sounds) comprising at least one standard stimulus, which provides a base pattern for the sequence and at least one novel deviant stimulus, which serves to engage the child's (or adult's) brain by its novelty as compared to the standard stimulus, wherein the at least one novel deviant stimulus differs from the standard stimulus by at least one of amplitude, frequency, pitch, pattern and/or duration.

Figure 2:
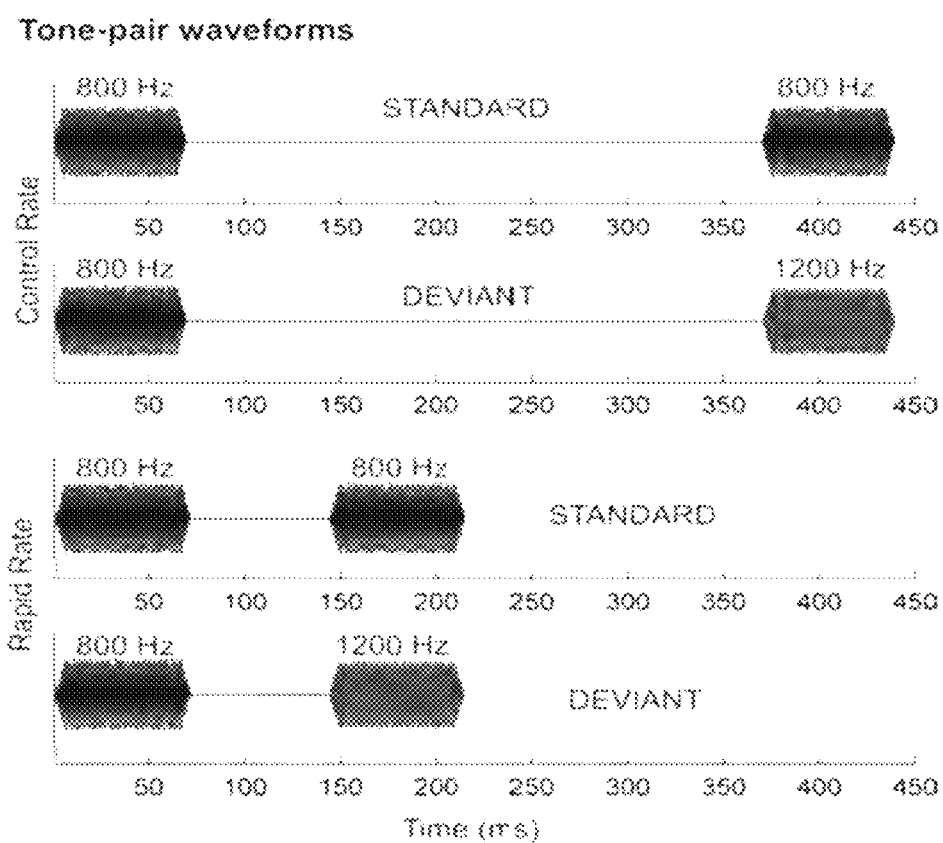
FIG. 2 illustrates exemplary tone-pair waveforms that include standard tones and novel deviant tones in accordance with the disclosure.

For example, FIG. 2 shows an example of a complex tone pair contrast at two different ISIs or rates that include "standard" tones and "novel" deviant tones that differ by frequency, The standard stimulus and the at least one novel stimulus are combined into an auditory sequence such that the proportion of standard to novel sounds is 90/10, 80/20, 70/30 or 60/40 and the auditory sequence is constructed with the at least one novel stimulus occurring within a pseudo-randomized interval (within about 300 ms to about 3 sec) after the at least one standard stimulus. This pseudo-randomly constructed sequence is then layered into the carrier sound envelope.

Figure 3:
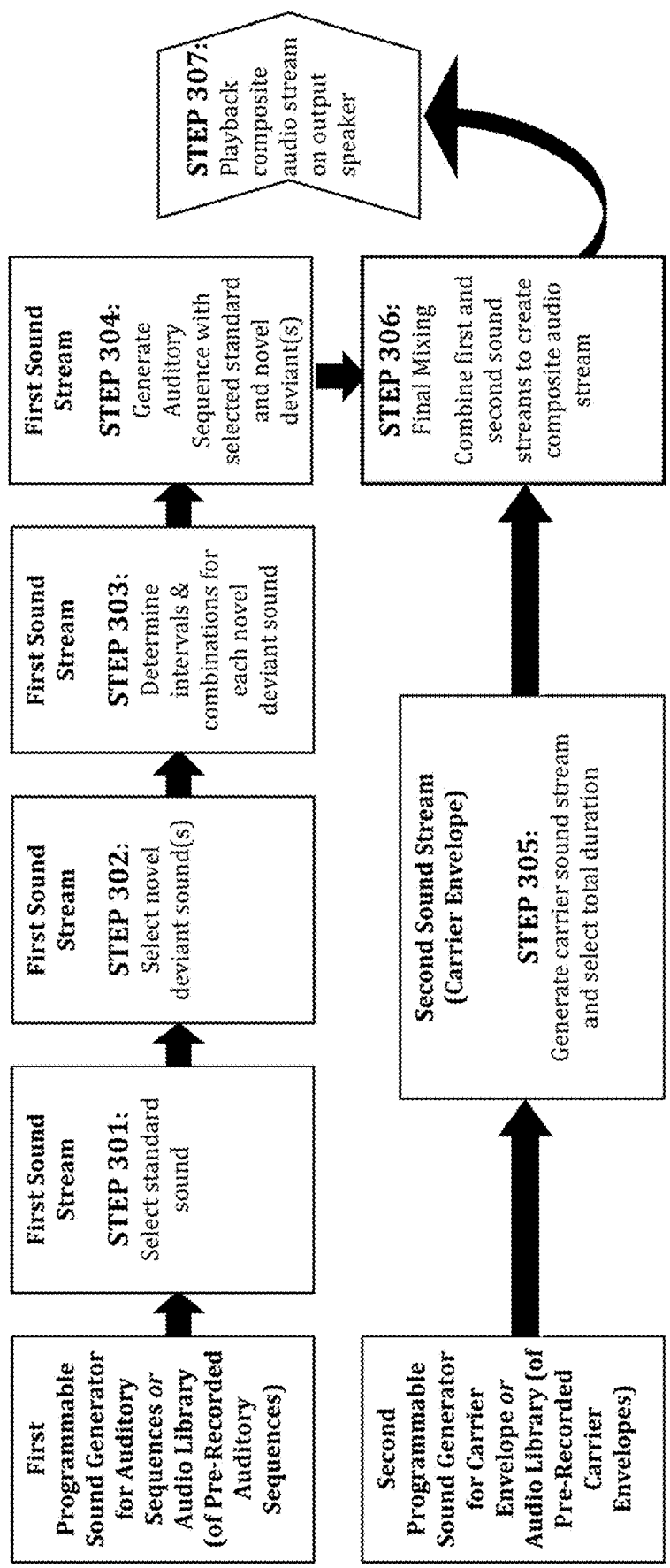
FIG. 3 is a flowchart that illustrates a method by which a composite output audio signal is produced in accordance with the disclosure.

FIG. 3 is a flowchart that illustrates a method in accordance with the disclosure for creating a composite audio output by mixing a first sound stream (an "auditory sequence") that includes a "standard" repeating sound and a contrasting infrequently presented "novel" deviant sound (or sounds) with a second sound stream of a carrier envelope. In FIG. 3, a standard sound is selected at step 301. The standard sound may be selected from the output of a first programmable sound generator or audio library. In the case of an audio library, the library may contain a plurality of pre-recorded auditory sequences. The selected standard sound is an audio signal having a temporal duration ranging from 2 to 300 ms, which is the range that maps onto phonemes, the sounds of language. Next, a novel deviant sound is selected at step 302. The selected novel deviant sound differs from the selected standard sound in one or more of the following characteristics: amplitude, frequency, duration, modulation and/or pattern including interspersed gaps, transitions or ISIs within each auditory signal. Then, at step 303, pseudorandom timings are used to determine intervals and combinations for each novel deviant sound (ranging from about 300 ms to about 3 sec) relative to the standard sound. Finally, at step 304, the novel deviant sounds are combined with the standard sounds according to the pseudorandom timings determined in step 303 to create an Auditory Sequence.

Meanwhile, at step 305, a carrier envelope is generated from the output of a second programmable sound generator or audio library, and the duration of the envelope is selected to produce a Second Sound Stream. In the case of an audio library, the library may contain a plurality of pre-recorded carrier envelopes. The generated carrier signal is a structured mixed-frequency carrier sound stream having a continuous, rhythmic variation of selected parameters. For example, the carrier envelope may contain sounds that mimic naturally occurring or constructed sound scenes (e.g., crickets and birds, ocean waves, wind, tonal music patterns, etc.) that have a variability and range. While the frequency range of the selected carrier depends on the type of carrier sound stream used (for example, ocean wave types of sounds will vary in a different range than tonal music patterns), that range must be between 40 and 10,000 Hz. The carrier sound stream is selected as having a duration of between 2 to 10 minutes, which will be the total duration of the composite sound stream sequence before repeating.

At step 306, the First Sound Stream is layered onto the Second Sound Stream while preserving the integrity of the First Sound Stream, thereby generating a composite sound stream of chosen length which, in step 307, is then output to an output speaker. Of course, the generated composite audio stream may be dynamically altered separately through control of a signal processor comprised of a digital microprocessor or microcomputer (not shown).

Also, as in the embodiment of FIG. 3, the composite output audio steam may be transmitted and played "on the fly" to an output speaker in real time. Alternatively, in other embodiments, the composite output audio stream may be recorded on a recordable medium and played back through any suitable playback device at a later time.

Consistent with the capabilities and sensitivities of the developing brain, all sounds in both the auditory sequence and carrier envelope are presented at 75 db or lower in intensity and implemented at frequencies ranging from 40 to 10,000 Hz. Further, the sounds presented (both standard and novel deviant sounds, as further discussed below) are constructed with a particular internal structure that provides language-like acoustic cues with differing acoustic contrasts, which capture the brain's attention and thus help the child's brain to fine-tune tonotopic acoustic maps.

In certain embodiments, the invention may be implemented in a version that includes a sleep soother or other multimodal device that displays light patterns that are synchronized with the audio recording to improve its ability to tune the brain to pay attention to tens of milliseconds variations in environmental sounds, a critical cognitive function that is developed at early ages.

In certain embodiments, the system may also include a device or system of devices capable of either playing a pre-recorded sequence of the type described above or which is capable of producing and emitting such an auditory sequence.

In certain embodiments, the system may include components configured to receive a plurality of audio signals and capable of generating or playing a plurality of monophonic audio streams and one or more sets of acoustic contrasts to associate with each of the audio streams, (i.e., the resultant recording, software program or system producing a digital audio stream) on the delivery device, for example, a speaker or a speaker array or other multi-modal audio device such as a smart speaker, mobile phone, tablet or computer (with or without earphones).

The one or more devices may include, or be in communication with, one or more processing and or playback elements or devices (e.g., microprocessors, processors, processing circuitry, etc.). In certain exemplary embodiments, the processing element or digital audio stream or recording or software product is embedded in or delivered to a child's or (adult's) soothing device, and may be embodied as one or more integrated circuits, application specific integrated circuits (ASICs), interface programmable logic arrays (PLAs) or the like. The processing element or digital audio stream or recording or software product may be configured to execute instructions stored in volatile or non-volatile memory and may be capable of performing steps or operations according to the exemplary embodiments discussed including synchronization with light patterns spatiotemporally related to the sound streams or scenes.

FIGS. 4a-c and FIG. 5, characterized by the following detailed audio narrative, disclose an example of a spatiotemporally organized auditory sequence that contains a plurality of non-linguistic sounds (repeated standards and novel deviants) organized algorithmically in a complex pattern designed to mimic the critical timing and structure of naturally occurring linguistic acoustic cues. These discrete sounds are embedded within a structured carrier sound envelope to produce a developmentally beneficial sound environment. These sounds are designed to capture the brain's attention and more specifically to stimulate and fine-tune the developing tonotopic acoustic maps that are crucial to emerging language.

Figure 4A:
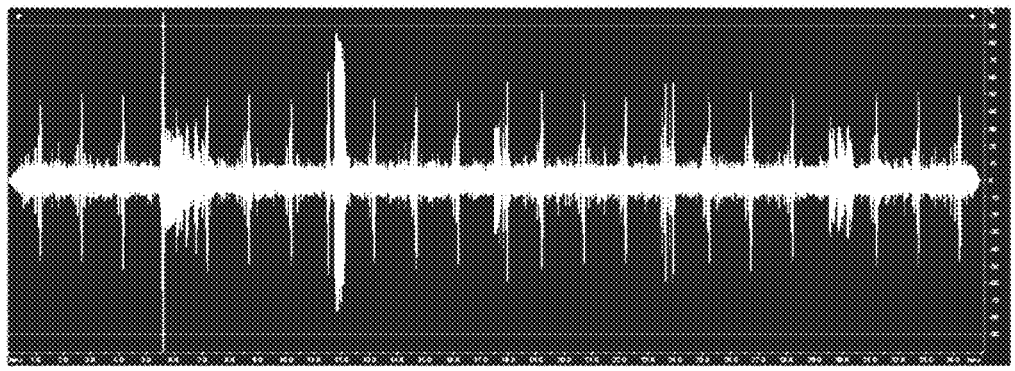
FIGS. 4*a-c* illustrate an exemplary auditory sequence, "Birds with Stream," which includes a plurality of standard sounds followed at pseudorandomly specified intervals and combinations by a plurality of novel deviant sounds embedded in a carrier sound envelope in accordance with the disclosure.
Figure 4B:
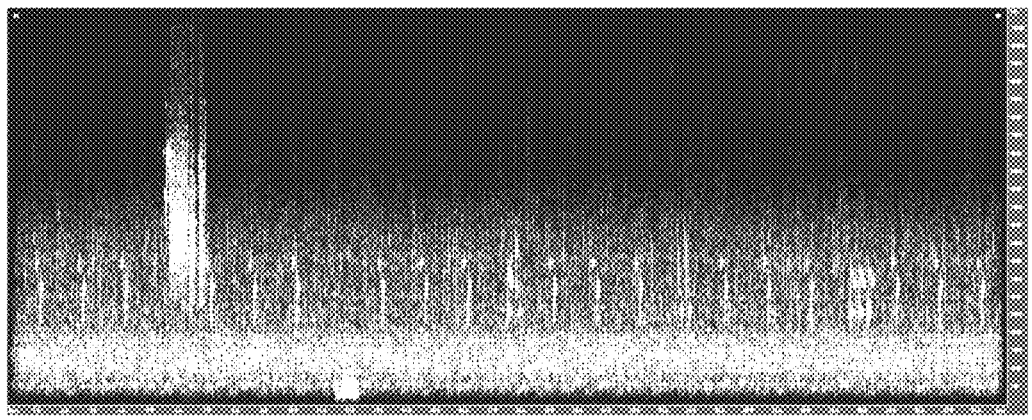
Figure 4C:
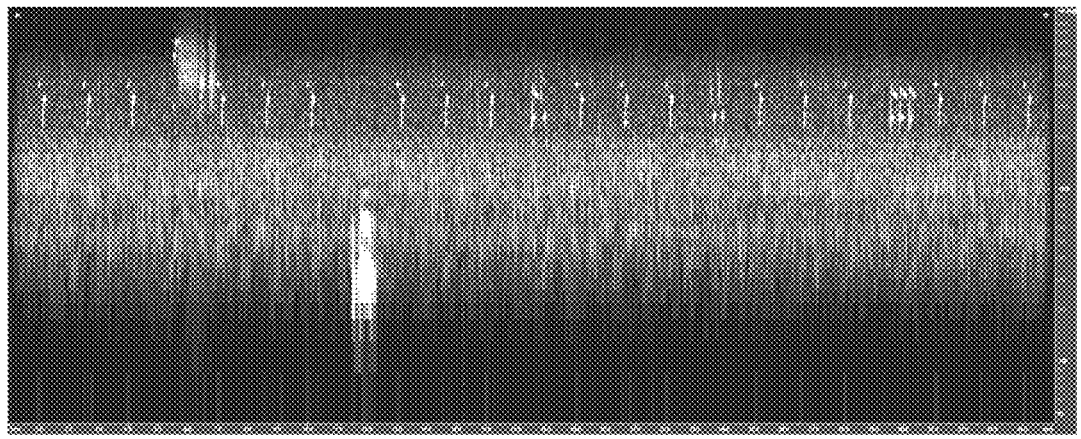

FIGS. 4a-c show a 35-second constructed auditory sequence, "Birds with Stream," which includes a plurality of standard sounds followed at pseudorandomly specified intervals and combinations by a plurality of novel deviant sounds (birds, crickets, etc.) embedded in a carrier sound envelope (mimicking running water). FIG. 4a is a frequency vs. time plot of a complex combined waveform of the "Birds with Stream" sequence. FIG. 4b shows a frequency vs. time linear spectrogram of "Birds with Stream." A spectrogram is a standard sound visualization tool, showing the distribution of energy in both time and frequency, and is simply an image formed by the magnitude of a Fourier transform, normally on a log-intensity axis (e.g., dB). FIG. 4c is a frequency vs. time log spectrogram of "Birds with Stream."

Narrative of Exemplary Audio Sequence

"Birds with Stream" is one example of a constructed sound sequence that was made using the methods disclosed herein. This exemplary embodiment is a 35-second combined audio scene that consists of two basic components, Sound Stream #1 and Sound Stream #2.

Component (Sound Stream) #1

Component (Sound Stream) #1, at an amplitude of 50%, consists of a varying overlay (the auditory sequence) that is superimposed onto Component (or Sound Stream) #2 (the carrier envelope). Component #1 is comprised of a patterned sequence that includes a "standard" sound that repeats approximately every 1500 ms, except at pseudorandom intervals when the standard sound is replaced with one or more "novel" deviant sound bursts.

Component #1's standard sound consists of a 260 ms burst of sound that mimics the sound of a bird chirp and is composed of the following segments:

65 ms in which the fundamental frequency rises linearly from 3850 Hz to 3950 Hz;

70 ms of silence;

60 ms of two frequency shifts of approximately equal amplitude: 2350 to 2400 Hz, and 2550 to 2600 Hz, and 65 ms with a fundamental frequency of 3400 Hz.

Component #1's novel deviant sounds consist of the following segments occurring at the pseudorandomly selected intervals noted below.

At 5.5 seconds, at an amplitude of 100%, Component #1's standard sound is replaced with a 1500 ms sound burst that mimics the sound of a bird flutter. The segments include:

60 ms in which the fundamental frequency rises linearly from 2800 Hz to 3000 Hz then falls to 2700 Hz, which includes a second harmonic of approximately equal amplitude;

60 ms of white noise, filtered to include only 3500 Hz to 7000 Hz, repeated 15 times; and 270 ms of white noise, filtered to include only 3000 Hz to 6000 Hz, repeated 2 times.

At 11.5 seconds, at an amplitude of 50%, Component #1's standard sound is replaced with a 650 ms sound burst that mimics the sound of a dog barking. The segments include:

100 ms in which the fundamental frequency rises linearly from 250 Hz to 300 Hz then falls linearly to 250 Hz, which includes a second harmonic of approximately equal amplitude;

150 ms of silence; and 400 ms in which the fundamental frequency rises linearly from 250 Hz to 300 Hz then falls linearly to 250 Hz, which includes a second harmonic of approximately equal amplitude.

At 17.5 seconds, at an amplitude of 60%, Component #1's standard sound is replaced with a 530 ms sound burst that mimics the sound of a bird chirp. 85 ms in which the fundamental frequency rises exponentially from 2500 Hz to 3500 Hz, then continues at 3500 Hz. The segments include:

40 ms with a fundamental frequency of 2600 Hz;

150 ms in which the fundamental frequency falls linearly from 3500 Hz to 3400 Hz;

25 ms of silence;

75 ms in which the fundamental frequency falls linearly from 5000 Hz to 3000 Hz;

50 ms of silence;

75 ms with a fundamental frequency of 2600 Hz; and 30 ms with a fundamental frequency of 1700 Hz.

At 23.5 seconds, at an amplitude of 55%, Component #1's standard sound is replaced with a 530 ms sound burst that mimics the sound of a double bird chirp. The segments include:

65 ms in which the fundamental frequency falls from linearly 5000 Hz to 3000 Hz then rises linearly to 4500 Hz;

50 ms of silence;

125 ms with a fundamental frequency of 2500 Hz; and 25 ms of silence.

At 29.5 seconds, at an amplitude of 30%, Component #1's sound burst is replaced with a 900 ms sound burst that mimics the sound of a triple bird chirp. The segments include:

90 ms in which the fundamental frequency rises linearly from 2400 Hz to 3600 Hz;

50 ms with a fundamental frequency of 2500 Hz;

130 ms in which the fundamental frequency falls linearly from 3500 Hz to 3400 Hz; and 30 ms of silence.

Component (Sound Stream) #2

Component (Sound Stream) #2, which is the carrier sound envelope, is at an amplitude of 15%. This sound envelope mimics the sound of running water and continues throughout the auditory sequence. The waveform is a self-similar fractal, which is scale invariant across its spectrum range of approximately 100 Hz to 7,000 Hz, with a broad 5 dB amplitude peak centered at 1000 Hz. Within any slice of its spectrum, the envelope has a punctate distribution in time, each containing a large number of high and low amplitude instances which occur randomly.

Figure 5:
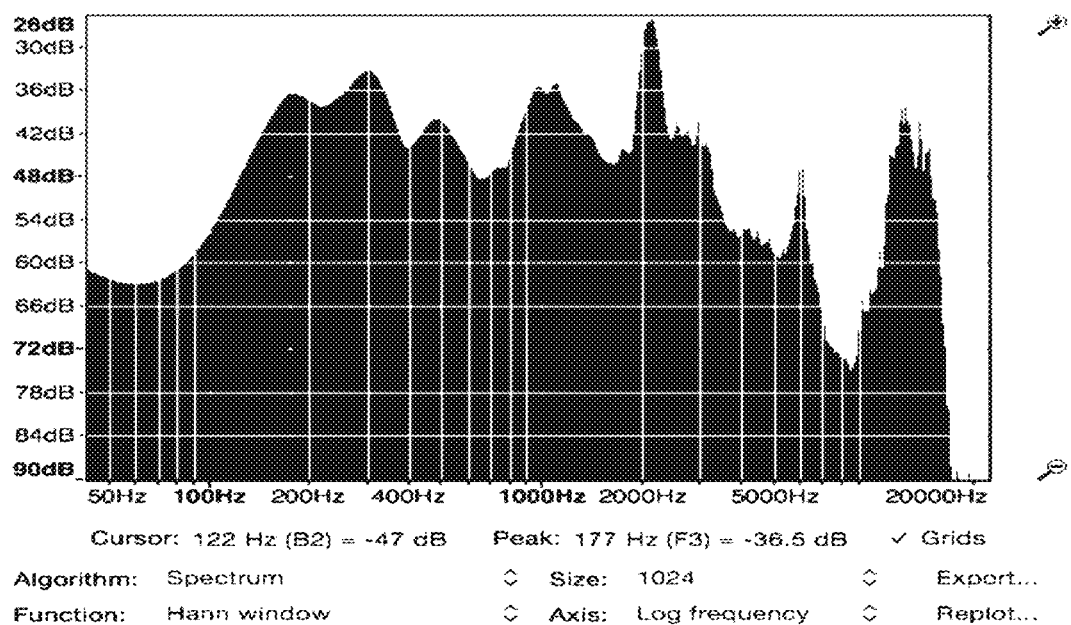
FIG. 5 illustrates a plot spectrum of "Birds with Stream," constructed in accordance with the disclosure, decomposed using a Fast Fourier Transform (FFT) to which a Hann Window has been applied. This window is used on signals that are captured in a non-periodic manner to reduce spectral leakage and get closer to the actual periodic results.

FIG. 5 shows an alternate plot spectrum of "Birds with Stream", which is constructed in accordance with the disclosure. This figure demonstrates the variability and periodicity of the ongoing combined sound stream "Birds with Stream" using a Hann Window. More specifically, here the exemplary sound stream is decomposed using a Fast Fourier Transform (FFT) to which a Hann Window has been applied. A Hann window is used on signals that are captured in a non-periodic manner to reduce spectral leakage and allow a display that is closer to the actual periodic results.

Additional embodiments of spatiotemporally organized non-linguistic auditory sequences are described below. These embodiments consist of complex sounds and patterns specifically constructed according to the algorithmic rules for the invention's sounds, to tune the developing brain to detect and pay attention to critical tens of milliseconds sound transitions.

These complex patterned sounds are then embedded in a structured but varying carrier sound stream. The patterned acoustic cues help the child to identify sound variations that "might be language" thus supporting and enhancing efficient and eventually automatized mapping of the sounds of his/her native language.

Figure 1B:
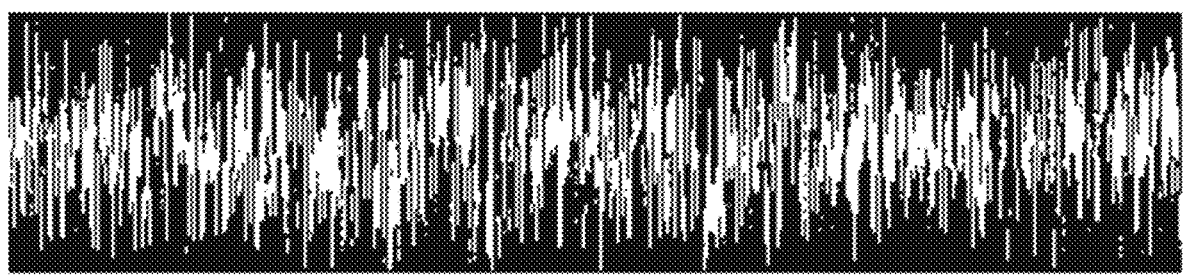
Figure 6A:
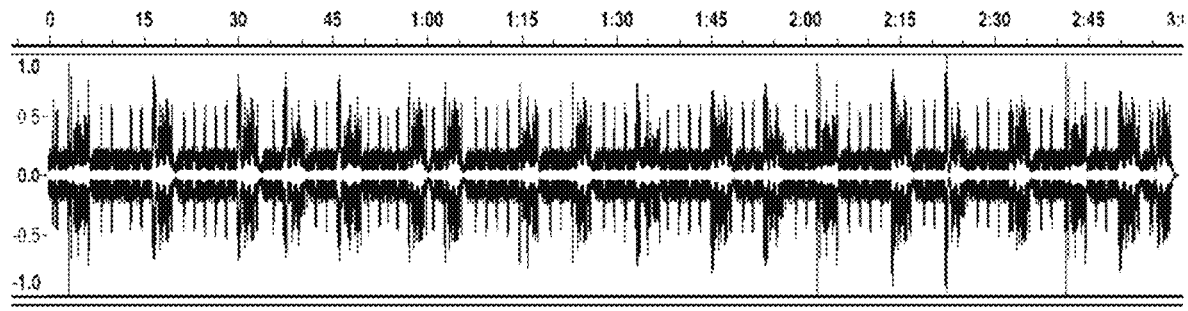
FIGS. 6*a-d* illustrate additional exemplary auditory sequences.
Figure 6B:
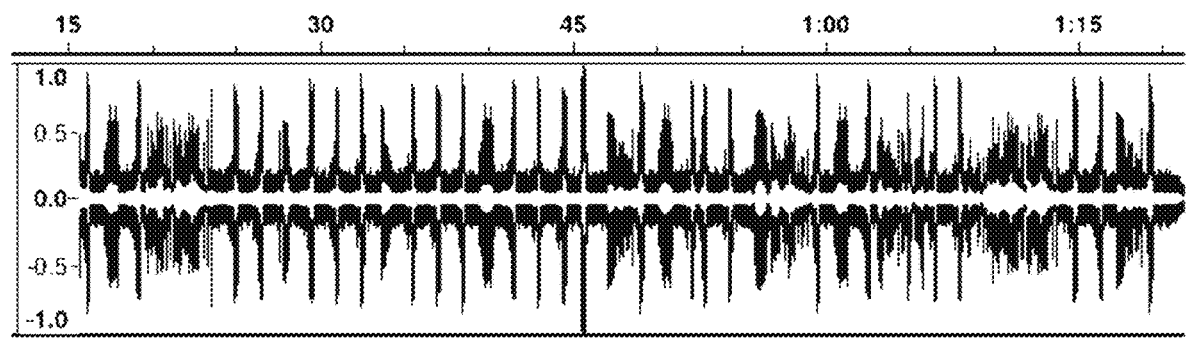
Figure 6C:
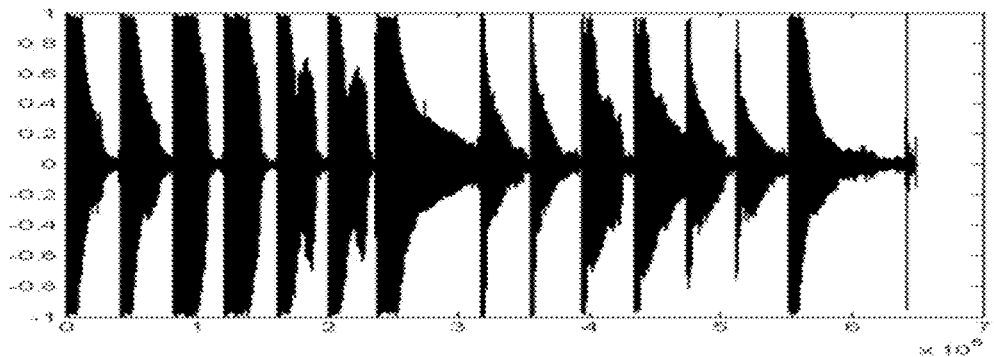

Spectrograms for white noise (discussed above) and for the popular children's song "Twinkle, Twinkle, Little Star" are also shown for comparison (see FIGS. 1a-b and 6c). As discussed above, white noise can be harmful to a child's language development, particularly when present in the environment for extended periods of time. In contrast, children's nursery rhymes and lullabies have some of the spatiotemporally organized structure developing brains require and do present differing, but most often predictable, acoustic contrasts which serve to capture the developing brain's attention. Thus they are in general engaging and fun and, although not optimal, certainly not harmful in large doses as has been shown for continuous white noise.

FIGS. 6a and 6b show time vs. frequency spectrograms of additional embodiments of constructed sound sequences "Owl, Frogs, Crickets with Stream" and "Nature Mix with Stream," respectively. Like the "Birds with Stream" embodiment of a constructed sound sequence discussed above, the "Owl, Frogs, Crickets with Stream" and "Nature Mix with Stream" constructed sound sequences are additional examples of constructed sound sequences within the scope of the present invention. Both sequences include a plurality of standard sounds followed at specified intervals by a plurality of novel deviant sounds (that sound like owls, frogs, crickets, birds etc.) which are embedded in a carrier sound envelope (in these embodiments mimicking running water).

Figure 6D:
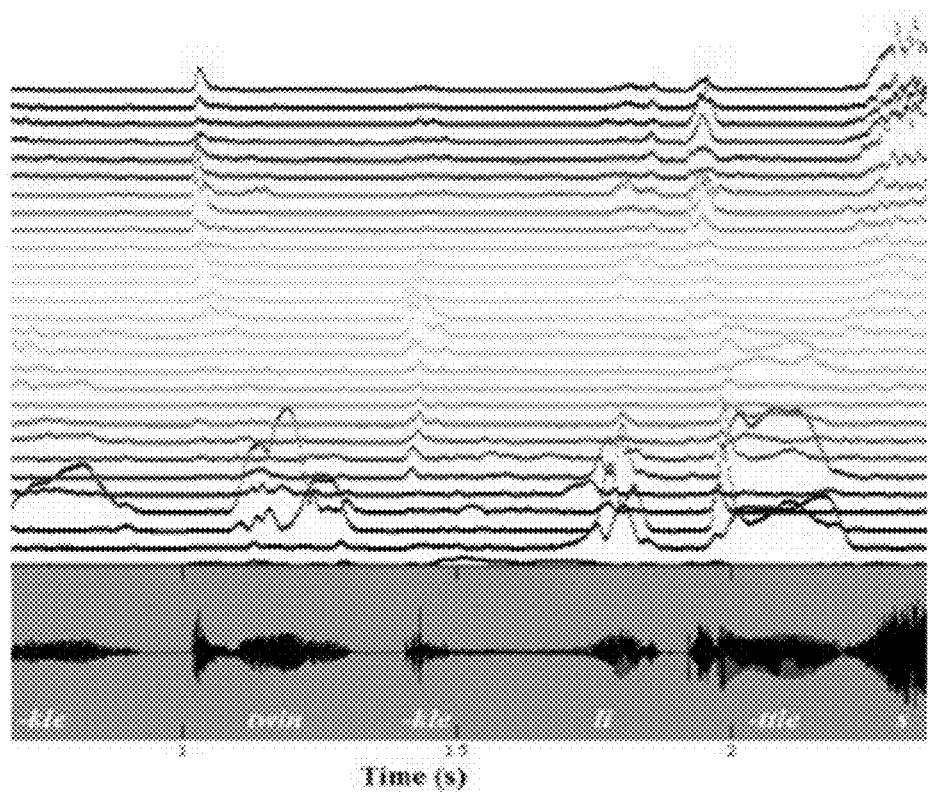

FIGS. 6c and 6d illustrate comparative examples of the children's song "Twinkle, Twinkle, Little Star." FIG. 6c shows a 28-second segment of the complex waveform of "Twinkle, Twinkle, Little Star." Compared to the spectrograms of FIGS. 6a and 6b, the spectrogram of FIG. 6c reveals a greater predictability of acoustic contrasts. FIG. 6d shows a 28-channel spectral analysis, using a Short-time Fourier transform (STFT), of 2.5 seconds of the children's song "Twinkle, Twinkle, Little Star" for comparison purposes. FIG. 6d similarly reveals the predictable and repetitive nature of acoustic contrasts across the frequency channels.

We claim:

1. A method of passively supporting the development and maintenance of language processing capabilities in a listener, comprising the steps of:

(a) constructing a composite audio signal comprising:

(i) a background sound carrier envelope; and (ii) an auditory sequence consisting of a series of a plurality of standard auditory signals and a plurality of novel deviant auditory signals;

wherein each of the plurality of standard auditory signals varies between about 2 to 300 ms in duration and about 40-10,000 Hz in frequency, and all auditory signals are 75 dB or lower, and wherein a pseudorandom number of at least one of the plurality of novel deviant auditory signals is presented at pseudorandom intervals within about 300 ms to about 3 sec of at least one of the plurality of standard auditory signals to construct the auditory sequence and the auditory sequence is then layered into the background sound carrier envelope to form the composite audio signal, wherein each novel deviant auditory signal differs from the standard auditory signal that immediately precedes it by at least one of amplitude, frequency, pitch, pattern and/or duration; and (b) playing back the composite audio signal on an audio playback device, wherein the played-back composite audio signal provides a sound enhancement environment that passively benefits the language processing capabilities in the listener.

2. The method of claim 1, wherein the listener is a child and the sound enhancement environment supports pre-linguistic brain development in the listener.

3. The method of claim 1, wherein the plurality of novel deviant auditory signals includes a first novel deviant auditory signal that is followed by a second (or more) novel deviant auditory signal(s), wherein said second (or more) novel deviant auditory signal(s) differs from said first novel deviant auditory signal in at least one of amplitude, frequency, pitch, pattern and/or duration.

4. A method of passively supporting the development and maintenance of language processing capabilities in a listener, comprising the steps of:
(a) constructing a composite audio signal comprising:
  (i) a background sound carrier envelope; and
  (ii) an auditory sequence consisting of a series of a plurality of standard auditory signals and a plurality of novel deviant auditory signals;
    wherein each of the plurality of standard auditory signals varies between about 2 to 300 ms in duration and about 40-10,000 Hz in frequency, and all auditory signals are 75 dB or lower, and
    wherein a pseudorandom number of at least one of the plurality of novel deviant auditory signals is presented at pseudorandom intervals within about 300 ms to about 3 sec of at least one of the plurality of standard auditory signals to construct the auditory sequence and the auditory sequence is then layered into the background sound carrier envelope to form the composite audio signal, wherein each novel deviant auditory signal differs from the standard auditory signal that immediately precedes it by at least one of amplitude, frequency, pitch, pattern and/or duration;
(b) storing the composite audio signal on a recordable medium; and
(c) playing back the composite audio signal from the recordable medium on an audio playback device, wherein
  the played-back composite audio signal provides a sound enhancement environment that passively benefits the language processing capabilities in the listener.

5. The method of claim 4, wherein the listener is a child and the sound enhancement environment supports pre-linguistic brain development in the listener.

6. An apparatus for playing back a pre-recorded audio signal that passively supports the development and maintenance of language processing capabilities in a listener, said apparatus comprising:
a receiver capable of receiving and playing back a composite audio signal from a pre-recorded medium, wherein said composite audio signal comprises:
  (i) a background sound carrier envelope having a duration ranging from 2 to 10 minutes;
  (ii) an auditory sequence consisting of a series of a plurality of standard auditory signals and a plurality of novel deviant auditory signals;
    wherein each of the plurality of standard auditory signal varies between about 2 to 300 ms in duration and about 40-10,000 Hz in frequency, and all auditory signals are 75 dB or lower, and
    wherein a pseudorandom number of at least one of the plurality of novel deviant auditory signals is presented at pseudorandom intervals within about 300 ms to about 3 sec of at least one of the plurality of standard auditory signals to construct the auditory sequence and the auditory sequence is then layered into the background sound carrier envelope to form the composite audio signal, wherein each novel deviant auditory signal differs from the standard auditory signal that immediately precedes it by at least one of amplitude, frequency, pitch, pattern and/or duration, and
  the composite audio signal is looped repeatedly to form a looped composite audio signal; and
a speaker for outputting said looped composite audio signal.

7. A method of recording a composite audio signal that passively supports the development and maintenance of language processing capabilities in a listener, the method comprising:
(i) generating a background sound carrier envelope having a duration ranging from 2 to 10 minutes;
(ii) generating an auditory sequence consisting of a series of a plurality of standard auditory signals and a plurality of novel deviant auditory signals;
  wherein each of the plurality of standard auditory signals varies between about 2 to 300 ms in duration and about 40-10,000 Hz in frequency, and all auditory signals are 75 dB or lower, and
  wherein a pseudorandom number of at least one of the plurality of novel deviant sound is presented at pseudorandom intervals within about 300 ms to about 3 sec of at least one of the plurality of standard signals to construct the auditory sequence;
(iii) layering the auditory sequence into the background sound carrier envelope to form a composite audio signal, wherein each novel deviant sound differs from the standard signal that immediately precedes it by at least one of amplitude, frequency, pitch, pattern and/or duration; and
(iv) storing said composite audio signal on a recordable digital medium.

* * * * *